United States Patent
Khait et al.

(10) Patent No.: US 10,357,144 B2
(45) Date of Patent: Jul. 23, 2019

(54) METHOD AND CIRCUIT FOR MUTING ELECTROMAGNETIC INTERFERENCE DURING MANEUVERING OF A DEVICE

(71) Applicants: GIVEN IMAGING LTD., Yoqneam (IL); ENAV MEDICAL LTD., Yokneam Ilit (IL)

(72) Inventors: Semion Khait, Tiberias (IL); Abraham Roth, Kefar Hasidim (IL)

(73) Assignee: GIVEN IMAGING LTD., Yoqneam (IL)

( * ) Notice: Subject to any disclaimer, the term of this patent is extended or adjusted under 35 U.S.C. 154(b) by 951 days.

(21) Appl. No.: 14/774,725

(22) PCT Filed: Mar. 13, 2014

(86) PCT No.: PCT/IL2014/050291
§ 371 (c)(1),
(2) Date: Sep. 11, 2015

(87) PCT Pub. No.: WO2014/141285
PCT Pub. Date: Sep. 18, 2014

(65) Prior Publication Data
US 2016/0038009 A1    Feb. 11, 2016

Related U.S. Application Data

(60) Provisional application No. 61/784,006, filed on Mar. 14, 2013.

(51) Int. Cl.
*A61B 1/00* (2006.01)
*A61B 1/04* (2006.01)
(Continued)

(52) U.S. Cl.
CPC .......... *A61B 1/00158* (2013.01); *A61B 1/041* (2013.01); *A61B 5/062* (2013.01);
(Continued)

(58) Field of Classification Search
CPC ... A61B 1/00158; A61B 1/041; A61B 5/0031; A61B 5/062; A61B 5/073; A61N 2/00;
(Continued)

(56) References Cited

U.S. PATENT DOCUMENTS 3,893,462 A      7/1975  Manning
4,410,926 A  *  10/1983  Hafner ...................... G01F 1/60
                                                              361/93.9
(Continued)

FOREIGN PATENT DOCUMENTS

CN           1043035 A      6/1990
WO      WO 2012/127469      9/2015

*Primary Examiner* — Thienvu V Tran
*Assistant Examiner* — Nicolas Bellido
(74) *Attorney, Agent, or Firm* — Pearl Cohen Zedek Latzer Baratz LLP (57) ABSTRACT

A switching circuit includes a first switch and a second switch respectively connecting a first terminal and a second terminal of an electrical coil to a positive terminal of a voltage source, a third switch and a fourth switch respectively connecting the first terminal and the second terminal of the electrical coil to a negative terminal of the voltage source, and a controller to control the switching circuit in a current control mode to alternate a voltage polarity of the voltage source to thereby control a magnitude and direction of the electrical current of the electrical coil, and to control the switching circuit in a current hold mode to disconnect the electrical coil from the voltage source and to short-circuit the electrical coil to maintain the magnitude and direction of the electrical current at the transition time when the switching circuit switched to the current hold mode.

17 Claims, 8 Drawing Sheets (51) Int. Cl.
    *A61B 5/07* (2006.01)
    *H05K 9/00* (2006.01)
    *A61B 5/06* (2006.01)
    *A61B 5/00* (2006.01)

(52) U.S. Cl.
    CPC ............ *A61B 5/073* (2013.01); *H05K 9/0071* (2013.01); *A61B 5/0031* (2013.01)

(58) Field of Classification Search
    CPC ........ A61N 2/004; A61N 2/006; A61N 2/008; A61N 2/02; A61N 2/12; B23Q 3/1543; F02D 2041/2027; H01F 13/00; H01F 2007/208; H01F 7/122; H01F 7/1805; H01H 47/00; H01H 47/04; H01H 47/22; H01H 47/32; H01H 47/325; H03K 5/04; H03K 7/08; H05K 9/0071
    USPC ............... 361/143, 145, 147, 152, 153, 154; 600/12, 13, 14
    See application file for complete search history.

(56) References Cited

U.S. PATENT DOCUMENTS

| | | | |
|---|---|---|---|
| 4,847,617 A | 7/1989 | Silvian | |
| 4,944,299 A | 7/1990 | Silvian | |
| 5,278,818 A * | 1/1994 | Zucker | G11B 5/02 360/66 |
| 5,946,182 A | 8/1999 | Hertzog et al. | |
| 6,031,740 A * | 2/2000 | Budmiger | G01F 1/60 363/131 |
| 6,123,658 A * | 9/2000 | Schweighofer | A61N 2/02 600/13 |
| 6,179,772 B1 | 1/2001 | Blackwell | |
| 7,118,529 B2 | 10/2006 | Glukhovsky et al. | |
| 7,268,516 B2 * | 9/2007 | Tankard | H02P 9/40 318/807 |
| 8,388,517 B2 | 3/2013 | Yoshizawa | |
| 2004/0236181 A1 * | 11/2004 | Honda | A61B 1/00032 600/118 |
| 2009/0010571 A1 | 1/2009 | Seki | |
| 2010/0174141 A1 * | 7/2010 | Gilad | A61B 5/6861 600/118 |
| 2012/0108883 A1 * | 5/2012 | Peterchev | A61N 2/02 600/14 |
| 2012/0271104 A1 | 10/2012 | Khait et al. | |
| 2012/0277529 A1 * | 11/2012 | Popescu | A61B 1/00029 600/109 |
| 2013/0053910 A1 | 2/2013 | Hareland | |
| 2014/0003418 A1 | 1/2014 | Khait et al. | |

* cited by examiner

METHOD AND CIRCUIT FOR MUTING ELECTROMAGNETIC INTERFERENCE DURING MANEUVERING OF A DEVICE

CROSS-REFERENCE TO RELATED APPLICATIONS

This application is a National Phase Application of PCT International Application No. PCT/IL2014/050291, entitled "METHOD AND CIRCUIT FOR MUTING ELECTROMAGNETIC INTERFERENCE DURING MANEUVERING OF A DEVICE", International Filing date Mar. 13, 2014, published on Sep. 18, 2014 as International Publication No. WO 2014/141285, which in turn claims priority from U.S. Patent Application No. 61/784,006, filed Mar. 14, 2013, all of which are incorporated herein by reference in their entirety.

FIELD OF THE INVENTION

The present invention generally relates to an in-vivo localization system and more specifically to a method for cancelling out, or muting, electromagnetic interference during maneuvering of an electromagnetic field maneuverable device, and to an electrical circuit implementing the electromagnetic interference cancelling/muting method.

BACKGROUND

In-vivo measuring systems are known in the art. Some in-vivo devices/systems that traverse the gastrointestinal (GI) system may include one or more imaging sensors, for imaging (e.g., capturing images of) the interior of the GI system, and/or sensors of other types. In-vivo devices may traverse the GI system by being pushed through the GI system by peristaltic force exerted by the digestive system, or by being maneuvered (e.g., magnetically). Some applications require knowing the current position and/or orientation (P&O) of the involved in-vivo device. For example, in order to magnetically maneuver an in-vivo device, for example in the GI system, the magnetic maneuvering system should know the current P&O (and the target P&O) of the in-vivo device in order to generate the correct steering magnetic fields. Therefore, a localization system may also be used in order to provide localization information to the magnetic maneuvering system, based on which the magnetic maneuvering system can maneuver the in-vivo device. A localization system may generate an alternating current ("AC") electromagnetic field that may be sensed by electromagnetic field sensors embedded in the in-vivo device. The P&O of the in-vivo device may be determined from the AC signals that the electromagnetic field sensors output.

An advanced maneuvering system may use an AC electromagnetic field and a direct current ("DC") electromagnetic field to maneuver devices in vivo. Operating an electromagnetic based localization system and an electromagnetic based maneuvering system at the same time may result in mutual interference between the two systems. For example, an external maneuvering AC magnetic field generated by the maneuvering system may have a negative side effect on the readout of the localization electromagnetic field sensors of the in-vivo device, and the external AC localization signal generated by the localization system may have a negative side effect on the maneuvering force that maneuvers the in-vivo device. Therefore, it is preferable that the two systems operate intermittently, with one system (e.g., the magnetic maneuvering system) operated while the other system (e.g., electromagnetic based localization system) is temporarily disabled, and vice versa. However, due to high currents that are usually required to generate maneuvering electromagnetic fields, the electromagnetic field, which may be generated by using a switching circuit/technique, may not be able to be shut down completely in time in, and for, the required time (e.g., when localization sensing takes place). Inability to shut down the maneuvering magnetic field completely on time may result in a residual electromagnetic field that causes electromagnetic field interference, thus to erroneous determination of the P&O of the in-vivo device.

Electrical currents of electromagnetic coils are often controlled by using pulse width modulation ("PWM"). However, using PWM results in switching frequency components superimposed on localization signals during localization time periods. Therefore, it would be beneficial to have a method that would enable a magnetic maneuvering system to steer an in-vivo device and a magnetic localization system to locate the in-vivo device without the maneuvering system interfering with the operation of the localization system.

SUMMARY

While using the maneuvering field is beneficial, in general, from the maneuvering system's standpoint, it would be beneficial to have a magnetic field maneuvering system that produces significantly reduced electromagnetic interference while maneuvering of an in-vivo device takes place.

A switching circuit may include a first switch and a second switch respectively connecting a first terminal and a second terminal of an electrical coil to a positive terminal of a voltage source, a third switch and a fourth switch respectively connecting the first terminal and the second terminal of the electrical coil to a negative terminal of the voltage source, and a controller to control the switching circuit. The controller may be configured to control the switching circuit in an electrical current control mode or period of time, or during a first period, to alternate a voltage polarity of the voltage source provided to the electrical coil, to thereby control a magnitude and direction/polarity of the electrical current flowing through, or via, the electrical coil. The controller may also be configured to control the switching circuit in an electrical current hold mode or period of time, or during a second period different from the first period, to disconnect the electrical coil from the voltage source and, concurrently, to short-circuit the electrical coil to maintain the magnitude and direction of the electrical current prior to the transition (or as part of the transitioning process) of the switching circuit to the electrical current hold mode or at the end of the first period. The controller may also be configured to transition the switching circuit between the first state (the electrical current control mode) and the second state (the electrical current hold mode), for example based on a control signal that the controller may generate or receive. Maintaining the electrical current (magnitude and direction) of the coil may include maintaining the coil's electrical current at a transition time between the current control mode and the current hold mode.

The switching circuit and its operation method may be used in an in-vivo device system where a magnetic field maneuvering system may use the current control mode to dynamically maneuver an in-vivo device, and the current hold mode to enable the in-vivo device to sense localization signals transmitted from a localization system without requiring to deal with electromagnetic field interference that are typically caused by switching circuits such as PWM-operated switching circuits.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures.

DETAILED DESCRIPTION

The description that follows provides various details of exemplary embodiments. However, this description is not intended to limit the scope of the claims but instead to explain various principles of the invention and the manner of practicing it.

Although embodiments of the invention are not limited in this regard, discussions utilizing terms such as, for example, "processing," "computing," "calculating," "determining," "inferring", "deducing", "establishing", "analyzing", "checking", or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information non-transitory storage medium that may store instructions to perform operations and/or processes. Unless explicitly stated, the embodiments of methods described herein are not constrained to a particular order or sequence of steps, operations or procedures. Additionally, some of the described method embodiments or elements thereof can occur or be performed at the same point in time.

An electromagnetic field sensing time window ("sensing window" for short) may be allocated in a work cycle of an in-vivo device for sensing electromagnetic localization signals, and possibly for processing the sensed signals. The in-vivo device may operate according to the work cycle. A "work cycle" may be a cycle or repeated time period, divided into time slots or periods, that includes a transmission period during which the in-vivo device transmits data (e.g., data frame; e.g., image frame, metadata, messages, etc.), for example to a receiver or to a data recorder, using a first communication channel, and an idle period during which the in-vivo device does not transmit data via the first communication channel. The sensing window may be wide enough to enable the in-vivo device to sense as many electromagnetic localization signals as required (e.g., an electromagnetic localization signal per coordinates of a coordinate system) to determine the position and/or orientation (P&O) of the in-vivo device, and narrow enough and located in the work cycle such that it would not interfere with other activities that the in-vivo device may be performing or involved in. Using localization signals may facilitate or be useful in determining the position of the in-vivo device in, or using, for example, the X, Y, Z coordinates system, or the polar coordinates system. "Localization signal" and "orientation signal" are hereinafter collectively referred to herein as "localization signal" and "sensing signal". The term "localization signal" may refer to a signal that represents a localization electromagnetic field generated by a localization signals source ("LSS") external to the in-vivo device and sensed by the in-vivo device, and to the signal that an electromagnetic field sensor of the in-vivo device outputs in response to it. Therefore, the term "localization signal" should be construed contextually.

A magnetic maneuvering unit (MMU) may use a magnetic field to maneuver devices in vivo. As described above, due to the high currents that are required to generate maneuvering magnetic fields, the magnetic field may be generated by using a switching technique such as the PWM switching technique or scheme. Due to the high currents and high switching frequency involved in using such a technique, the maneuvering system may not be able to be shut down completely when the localization system operates. Instead, the intensity of the magnetic field is decreased and 'locked' so as to momentarily 'freeze', or halt, the in-vivo device in space (e.g., retain the device at the same position and/or orientation) while the maneuvering system is shut down. Despite the maneuvering magnetic field's decreased intensity, aperiodic and periodic interference, which typically have a fundamental frequency and higher harmonies, are still superimposed on the localization signals and result in erroneous localization determination. Embodiments of the invention include an electrical switching circuit that is operated such that the electromagnetic interference during localization periods, or sensing windows, due to the PWM switching is mitigated, muted or eliminated, as described below, without requiring a frequency (or other) filter or extensive computation resources.

First, an example in-vivo device maneuvering and localization system is described in connection with FIG. 1. Then, an example in-vivo system is described in connection with FIG. 2 and, then, examples of a switching circuit and switching method are described. The in-vivo device maneuvering and localization system shown in FIG. 1 and the in-vivo system shown in FIG. 2 are more fully described in a PCT application, international publication number WO 2012/127469, the national stage application of which (US Published Application 2014-0003418) is incorporated by reference herein in its entirety.

Figure 1:
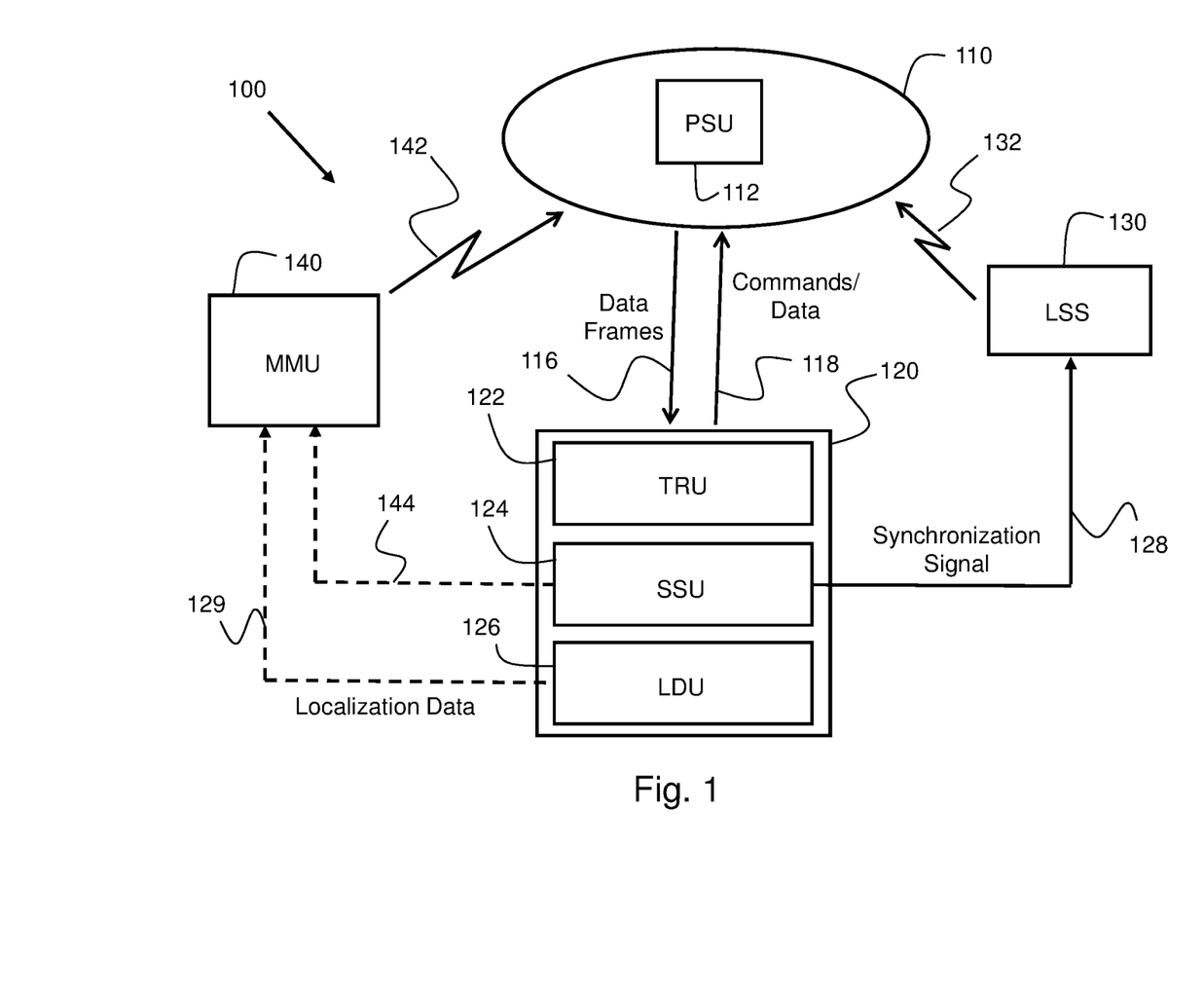
FIG. 1 is a block diagram of localization and maneuvering system for localizing and maneuvering an in-vivo device according to an embodiment of the invention.
Figure 2:
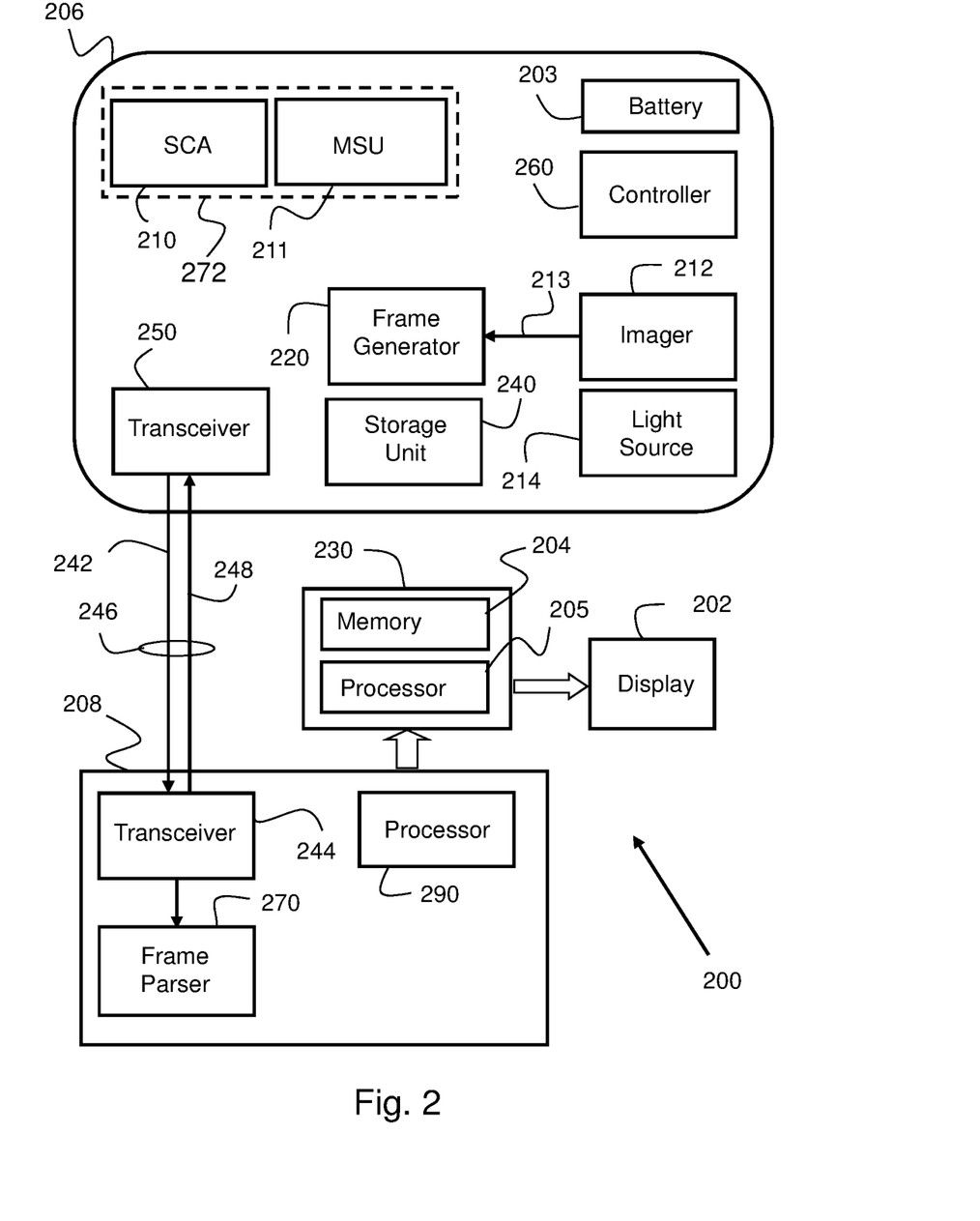
FIG. 2 is a block diagram of an in-vivo imaging system according to an embodiment of the invention.

FIG. 1 is a block diagram of localization and maneuvering system 100 for localizing and maneuvering an in-vivo device 110 according to an example embodiment. Maneuvering system 100, which is configured to maneuver in-vivo device 110 (to which a data recorder 120 may be functionally coupled, e.g., via a radio frequency link), may include a localization signals source ("LSS") 130 and a magnetic maneuvering unit (MMU) 140 for maneuvering in-vivo device 110 based on localization data that may be generated, or output, by in-vivo device 110 in response to localization signals that are transmitted, or emitted, from LSS 130 and sensed by in-vivo device 110. MMU 140 may include a set of electrical coils for generating magnetic maneuvering field(s), and a controller to control operation of the coils to generate a required magnetic maneuvering field.

In-vivo device 110 may be configured (e.g., it may include sensors) to sense a physical parameter in vivo. Temperature, pH, pressure, and impedance are example physical parameters that in-vivo device may sense. In-vivo device 110 may sense other physical parameters and/or be capable of performing various surgical operations in vivo. In-vivo device 110 may capture images (e.g., take pictures) in vivo (e.g., of various organs of the GI system/tract). In-vivo device 110 may include a transmitter for transmitting data, for example to data recorder 120, which data may be related to (e.g., represent) sensed physical parameter and/or to captured images. In-vivo device 110 may also include a position and steering unit ("PSU") 112. PSU 112 may include a sensing coil assembly ("SCA") for sensing (electromagnetic) localization signals that may be generated by an external localization system and induced in electromagnetic sensing coils of the SCA. An electromagnetic field sensing coil is an exemplary type of electromagnetic field sensor/transducer. The localization signals may be generated, for example, by localization signals source (LSS) 130. PSU 112 may also include a magnetic steering unit ("MSU") for maneuvering, or steering, in-vivo device 110 based on localization signals sensed by (induced in) the sensing coils of the SCA.

Data recorder 120 may include, among other items (e.g., receiver, data frame parser, data storage unit, processor, etc.), a localization data unit ("LDU") 126. Data recorder 120 may include a transceiver (such as the one shown in FIG. 2) for receiving data frames 116 from in-vivo device 110. Data recorder 120 may also include a transmitter for transmitting commands and/or data 118 to in-vivo device 110. Data recorder 120 may transmit a command to in-vivo device 110, for example, to change a mode of operation (e.g., an image capturing rate of an imager of the in-vivo device), or to update a parameter of the in-vivo device, etc. The mode or state of the device may be alternated by, for example, repeatedly or iteratively switching between states or modes. In-vivo device 110 may operate according to work cycles. A timing restoration unit ("TRU") 122 may be used to restore the work cycles of in-vivo device 110 that drive in-vivo device 110, and, based on the restored work cycles, to synchronize between in-vivo device 110, LSS 130 (the system generating/transmitting localization signals), and MMU 140 (the system generating the maneuvering magnetic field).

LSS 130 may transmit localization signals in short bursts, where each localization signal burst may include a number n of localization signals that may be spaced apart (e.g., they may be successive). For example, LSS 130 may transmit a localization signal burst for each coordinate of a coordinate system. In another example, each localization signal of a localization signal burst may be transmitted to sense a different coordinate. For example, LSS 130 may transmit, during a sensing window in a work cycle of in-vivo device 110, a localization signal burst that may pertain to the X-axis, then a localization signal burst that may pertain to the Y-axis, then a localization signal burst that may pertain to the Z-axis. LSS 130 may repeat the sequence of localization signal bursts for each work cycle, or for selected work cycles of the in-vivo device.

Concurrently to the restoration of the in-vivo device's clock signal and reference time by TRU 122, a synchronization signal unit ("SSU") 124 may produce a synchronization signal 128 that complies with the sensing window, and transfer the synchronization signal to LSS 130, for example via a communication cable or wirelessly. Synchronization signal 128 enables LSS 130 to correctly time the generation (and transmission) of one or more localization signals (in the form of electromagnetic field(s)). For example, LSS 130 may generate an electromagnetic field 132 at a time and for a duration set forth by, or complying with, synchronization signal 128, and therefore, in compliance with the restored sensing window(s), and therefore in compliance with the sensing window(s) originally used, or pre-allocated, by in-vivo device 110. Since the sensing window(s), which may be used by in-vivo device 110 during each work cycle or during selected work cycles, and the restored sensing window(s) used by data recorder 120 temporally overlap/match (within an operational margin), LSS 130 may generate/transmit localization signal 132 in time slot(s) during which in-vivo device 110 may read (e.g., by or after sampling) the electromotive force ("EMF") signals that the sensing coils assembly (SCA) of PSU 112, or another electromagnetic field sensor/transducer, may output in response to localization signal 132.

As a result of the SCA, or another electromagnetic field sensor, sensing the electromagnetic signals during a work cycle of in-vivo device 110, in-vivo device 110 may embed data, which represents the EMF signals, in a data frame that may be transmitted (e.g., to a data recorder) during a transmission period, for example, of the following work cycle. Data that represents the raw EMF signals induced in the in-vivo device, and any variant, manipulation, or derivative of such signals or data (e.g., data representing the actual coordinates, or position/orientation, of the in-vivo device) is referred to herein as "localization data" and "sensing data". As defined above, "localization data" may also refer to or include additional data that represents the orientation of the in-vivo device or enables to determine the orientation of the in-vivo device. Alternatively, localization data may be transmitted (e.g., to a data recorder) not by using the communication channel via which frames are transmitted, but by using a separate communication channel.

Localization data unit (LDU) 126 may include or use a processor and other components and units that are required to interpret, calculate, deduce, infer, or otherwise determine the current position, and, optionally, also the current orientation of in-vivo device 110 from, or by using, the localization data. After LDU 126 determines the P&O of in-vivo device 110, LDU 126 may transfer corresponding localization data 129 to another computing system. Localization data 129 may include data that represents the current position of in-vivo device 110, or the current orientation of in-vivo device 110, or both position and orientation of in-vivo device 110. The other computing system may, for example, display the P&O data (whether the raw data or a processed version thereof), and/or it may use past and current P&O data to display the route, or trajectory, traversed by the in-vivo device, and/or a point on a route representing the GI system, and/or it may use localization data 129 to maneuver, guide or steer in-vivo device 110.

LDU 126 may transfer position/orientation data 129 to MMU 140 as feedback in order for MMU 140 to generate a maneuvering magnetic field 142 to guide, steer, or maneuver, in-vivo device 110 to a new, target or desired position and/or to a new, target or desired orientation. That is, 'knowing' the current position of in-vivo device 110 (e.g., from position data 129), MMU 140 may generate a magnetic maneuvering signal 142 to maneuver in-vivo device 110 to a required, or target, position or orientation. PSU 112 may include a MSU that may include, for example, one or more permanent magnets. The permanent magnet(s) of the MSU may interact with magnetic signal 142 to produce magnetic forces and/or torques to steer the in-vivo device. MMU 140 may control the steering of in-vivo device 110 based, for example, on position/orientation signals that are provided by LDU 126 (e.g., position/orientation data 129).

Operation of MMU 140 may be synchronized to the operation of LSS 130 in order to ensure that MMU 140 and LSS 130 do not respectively generate maneuvering signal 142 and localization signal 132 at the same time. Synchronization signal 144 may be identical to synchronization signal 128 or a manipulation or derivative thereof. Synchronization signal 144 may cause MMU 140 to generate, for each work cycle of the in-vivo device, a signal 142 in the form of a short maneuvering signal (e.g., a 'maneuvering burst'), or a series of maneuvering bursts, shortly after a sensing window is terminated.

FIG. 2 shows an in-vivo imaging system 200 according to an example embodiment. While FIG. 1 references an in-vivo device (in-vivo device 110) that transmits data frames that may be related to or include any type of sensory data (e.g., pH data), FIG. 2 shows in-vivo device 110 with an imager as an example sensor, in which case in-vivo device 110 may be referred to as an "in-vivo imaging device" or an "in-vivo imager", and (data/image) frames transmitted by or from in-vivo device 110 may be referred to as "image frames" (although image frames may include also other types of data, including localization data and/or other types of sensory data). The systems of FIGS. 1 and 2 may have similar components and thus the system shown in FIG. 1 may have some or all of the elements shown in FIG. 2 and vice versa. In-vivo imaging system 200 may include an in-vivo device 206, a data recorder 208, a user workstation 230, which may be, for example, a workstation or personal computer, and a display 202 for displaying, for example, images and/or a video clip or moving image stream which is produced from images, and for displaying the position and/or orientation of the in-vivo device, etc. In-vivo device 206 may include some components of or some aspects of in-vivo device 110, and vice versa.

An in-vivo imaging device may include one or more imagers. By way of example, in-vivo device 206 includes one imager (e.g., imager 212). In-vivo device 206 may also include a light source 214 for illuminating a GI section/site/organ to be imaged, a frame generator 220 for producing an image frame for each captured image, a computer processor or controller 260, a storage unit 240 for storing, for example, data and executable instruction code or software, a transmitter or transceiver 250 for transmitting image frames and, optionally, for receiving data and/or commands from data recorder 208, and an electrical power source 203 for powering these components and circuits.

In-vivo device 206 may also include a position and steering unit (PSU) 272 (possibly similar to PSU 112). PSU 272 may include a sensing coil assembly (SCA) 210 for sensing localization signals generated, for example, by LSS 130 of FIG. 1. SCA 210 may include a number n of electromagnetic sensing coils for sensing, through electromagnetic induction, electromagnetic localization fields/signals, where n is an integer equal to or greater than 1 (e.g., n=3 sensing coils) that may be, for example, mutually perpendicular. Two sensing coils or more than 3 sensing coils may be used. Each electromagnetic sensing coil may be used to sense an electromagnetic field in a different direction/orientation. For example, one coil may be used to sense an electromagnetic field in the 'X' direction or in the Y-Z plane, another coil may be used to sense an electromagnetic field in the 'Y' direction or in the X-Z plane, etc.

In-vivo device 206 may also include a magnetic steering unit (MSU) 211 to magnetically maneuver in-vivo device 206, for example through interaction with magnetic fields which may be generated by a maneuvering system similar to magnetic maneuvering unit (MMU) 140 of FIG. 1. MSU 211 may include, for example, permanent magnet(s) that may interact with an externally generated magnetic signal (e.g., magnetic signal 142 of FIG. 1) to produce magnetic force(s) and/or magnetic torque(s) to steer in-vivo device 206 in a desired direction or to orient or position it in a desired orientation/direction.

Even though it is preferable that MMU 140 be shut down completely while sensing of localization signals by SCA 210 takes place, for the reasons specified above (e.g., high currents and switching used to generate the maneuvering magnetic field), MMU 140 may be operated such that it would still output a relatively high magnetic field, and, yet, it may do so without interfering with the generation and sensing of the localization signals.

Data representing, or derived from, the EMF signals induced in SCA 210 may be transmitted (242) by transmitter 250, for example to data recorder 208, by embedding the data in image frames and/or by using frames that may be dedicated to transfer of such data. Frames generator 220 may receive image data 213 that represents a captured image, and produce a corresponding image frame (or "frame" for short) that contains image data Controller 260 may operate, among other things, light source 214 to illuminate GI areas traversed by in-vivo device 206, and schedule the images capturing times accordingly. Controller 260 may temporarily store captured images and related image frames in data storage unit 240. Controller 260 may also perform various calculations and store interim calculation results in data storage unit 240. Controller 260 may also read the EMF output of SCA 210 at (during) the allocated sensing window(s) from which the position and/or orientation of in-vivo device 206 may be calculated or deduced (e.g., by controller 260 or by an external system; e.g., data recorder 208). Controller 260 may time the writing (e.g., adding, appending, or otherwise embedding) of localization data (e.g., the sensing coils readout or a manipulated version thereof) into the corresponding frame; e.g., into a frame that is to be transmitted, for example, some time or immediately after, or concurrently to, the reading of the output of the sensing coils. After frames generator 220 produces a frame for a captured image and embeds localization data in the frame, controller 260 may use transceiver 250 to wirelessly transfer 242 the frame to data recorder 208. Controller 260, by executing software or instructions, may carry out steps which are performed by frame generator 220, and other functions in in-vivo device 206, and thus may function as these units.

Data recorder 208 may also include a receiver or transceiver 244, a frame parser 270 and a processor 290 for managing them. Transceiver 244 may receive 242 a data frame corresponding to a particular captured image, and frame parser 270 may parse the data frame to extract the various data contained therein (e.g., image data, decimated image associated with the particular captured image, localization data, etc.).

User workstation 230 may include a display or be functionally connected to one or more external displays, for example to display 202. Workstation 230 may receive frames (e.g., image frames, localization frames, etc.) or images from data recorder 208 and present them in real-time, for example as live video, or produce a video stream that also contains P&O information that may also be displayed on, for example, display 202. Workstation 230 may include a memory (e.g., memory 204) for storing the frames transferred from data recorder 208 and possibly related metadata, and a processor (e.g., processor 205) for processing the stored frames and related data. Workstation 230 may display selected images or a video clip (e.g., a moving image stream) compiled from such images, e.g., to a human operator, health care or caregiving person, physician, etc.

Figure 3:
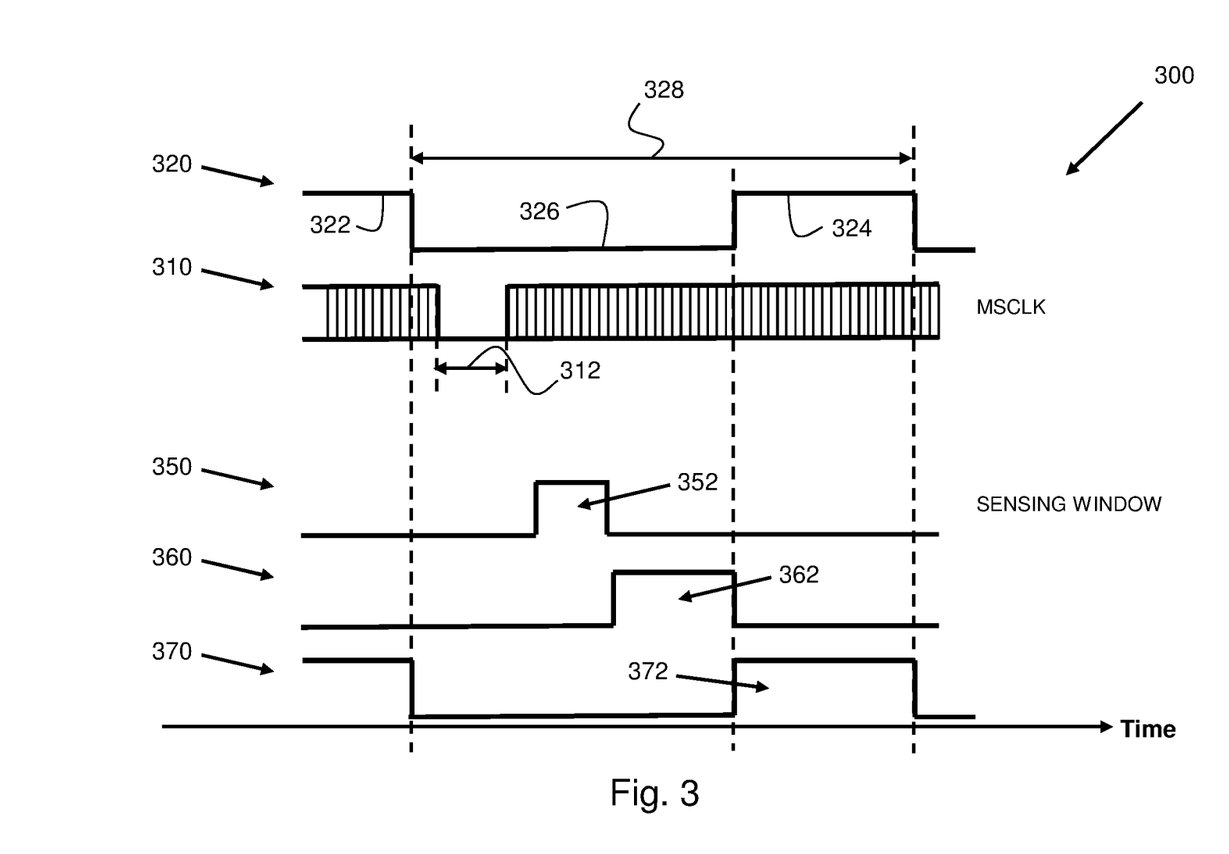
FIG. 3 schematically illustrates a timing diagram according to an embodiment of the invention.

FIG. 3 shows a timing diagram 300 used internally by an in-vivo device according to an example embodiment. Graph 310 is a master clock (MSCLK) signal. MSCLK signal 310 may be used internally by the in-vivo device to synchronize the activities performed by the in-vivo device. Graph 320 is a main signal that is timed based on MSCLK signal 310. That is, MSCLK signal 310 enables timing the logic value '1', or 'high' state, of main signal 320, as shown at 322 and 324, and the logic value '0', or 'low' state, of main signal 320, as shown at 326.

The duration of the high states of main signal 320 (e.g., high states 322 and 324) may be set to comply with the transmission period discussed above. The duration of the low states of main signal 320 (e.g., low state 326) may be set to comply with the idle periods discussed above. Time cycle $T_{CYCLE}$ 328, which is an example work cycle, includes, therefore, idle period 326 and transmission period 324. During idle period 326 the output of the clock generator that generates MSCLK signal 310 may be disabled for a time period 312 to improve the reception quality of commands and/or data from the data recorder and, in general, to reduce electrical noise in the in-vivo device.

Graph 350 is a sensing window signal. Sensing window pulse 352 may signal to the in-vivo device's controller a time slot (e.g., a sensing window) during which the in-vivo device may prepare to receive localization signals (e.g., from localization signals source (LSS) 130), process the localization signals, and store corresponding localization data in a storage unit (e.g., in storage unit 240).

Graph 360 is a window signal that may signal to the in-vivo device's controller a time slot (e.g., an imaging window) during which the in-vivo device may capture an image by, for example, activating, during window 362, the illumination source (e.g., light/illumination source 214) and the imager (e.g., imager 212), and executing related processes (e.g., image capturing and processing, storing image data, etc.).

Graph 370 is a frame signal signaling to the in-vivo device's controller a time slot (e.g., a transmission period 372) during which the in-vivo device may activate the transmitter (e.g., transmitter 250) to transmit a data frame (e.g., image frame). The data frame may include any combination of image data, localization data, prefix data bits, suffix data bits, and other types of data.

Pulse/window 352 (and like pulses/windows in other work cycles), pulse/window 362 (and like pulses/windows in other work cycles), and pulse/window 372 (and like pulses/windows in other work cycles) may be timed, for example, by counting pulses of a time clock.

Localization signals may be transmitted to the in-vivo device's SCA (e.g., SCA 210) during sensing window 352. In order to infer or deduce the P&O of the in-vivo device correctly/reliably, the magnetic maneuvering system that maneuvers the in-vivo device reduces the magnitude of the frequency harmonics of the maneuvering signal during the sensing windows (a sensing window per working cycle of the in-vivo device), as described below.

Figure 4:
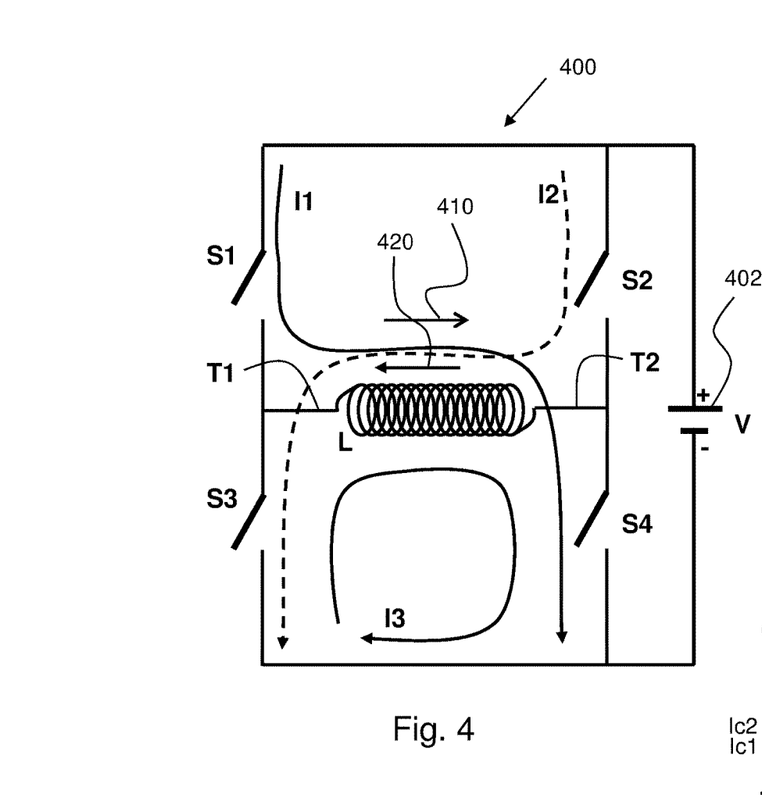
FIG. 4 is a schematic switching circuit according to an embodiment of the invention.

FIG. 4 schematically shows a switching circuit 400 for operating an electrical coil (L) according to an example embodiment of the invention. (A magnetic maneuvering system may include a plurality of coils similar to coil L, and each coil may be operated in a similar way, as described herein.) Switching circuit 400 may include a first switch, S1, and a second switch, S2 respectively connecting, or interposed between, a first terminal, T1, and a second terminal, T2, of an electrical coil, L, to/and a positive terminal, +V, of a voltage source 402 that powers coil L, and a third switch, S3, and a fourth switch, S4, respectively connecting, or interposed between, the first terminal (T1) and the second terminal (T2) of electrical coil L to/and a negative terminal, −V, of voltage source 402.

A controller (e.g., controller 810 in FIG. 8, or a similar controller) may be configured to switch or transition switching circuit 400 between an electrical current control mode ("control mode") and an electrical current hold mode ("hold mode"). During the current control mode or period, or during a first period, the controller may control switching circuit 400 to (timely) alternate a voltage polarity (e.g., positive to negative and vice versa) of voltage source 402 that is provided to electrical coil L, to thereby control a magnitude and direction of the electrical current of the coil's electrical coil. (In some embodiments, the magnitude of a current of the electrical coil may be controllable between tens of amperes to hundreds of amperes; e.g., between 15 amperes and 350 amperes.) Alternating of the polarity may include switching, e.g., repeatedly switching, the polarity e.g., from minus to plus to minus, etc. During the current hold mode or period, or during a second period different from the first period, the controller may control switching circuit 400 to disconnect (e.g., electrically disconnect) electrical coil L from the voltage source and to short-circuit the electrical coil (e.g., electrically connect one electrical terminal of the coil to the other electrical terminal of the coil) to maintain the magnitude and direction of the coil's electrical current at the end of the first period (e.g., at the transition time between the first period and the second period, or at the transition time between the current control mode and the current hold mode).

Referring to FIG. 4, when switches S1 and S4 are closed (and, at the same time, switches S2 and S3 are open), terminal T1 of coil L is connected to the positive terminal of the voltage source, and terminal T2 of coil L is connected to the negative terminal of the voltage source. Consequently, the electrical current of coil L is current IL which flows in a first direction, as shown at 410 (from the left hand side of the coil to the right hand side of the coil). After a predetermined time elapses, switches S1 and S4 are opened and switches S2 and S3 are closed to connect terminal T1 of coil L to the negative terminal of the voltage source and terminal T2 of coil L to the positive terminal of the voltage source. Consequently, the voltage polarity of the voltage source provided to coil L is reversed, causing the electrical current of coil L to be current I2, which flows in a second (opposite) direction, as shown at 420.

Switching circuit 400 may be operated as described above during a current control mode, or during a first period, to dynamically control the current of coil L, for example, to magnetically maneuver, for example, an in-vivo device. (The current control mode is further described below in connection with FIGS. 5 and 6.) Switching circuit 400 may also be operated during a current hold mode, or during a second period different from the first period, to maintain the current of coil L prior to the transition to the current hold mode, as described below, for example to facilitate sensing, by an in-vivo device, of localization signals that may be transmitted by a localization system, without requiring to deal with switching-induced electromagnetic interference. ("Facilitate sensing of localization signals" may include reducing the switching-induced electromagnetic interference during the period when the current hold mode is activated increases (improves) the signal-to-noise ratio ("SNR") involved in sensing localization signals, hence the accuracy with which the location and/orientation of the device is/are determined.)

Referring to FIG. 4, transitioning or switching into the current hold mode, or to the second period, may be achieved by simultaneously opening switches S1 and S2 and closing switches S3 and S4. The relationship between a voltage (v) of a coil and the coil's current (i) is given by equation (1):

$$v = L\left(\frac{di}{dt}\right) \quad (1)$$

where v is the coil's instantaneous voltage, L is the coil's reactance and i is the coil's instant current.

Opening switches S1 and S2 disconnects both terminals T1 and T2 of coil L from the voltage source (e.g., from the positive pole of the voltage source), and closing switches S3 and S4 short circuits coil L (electrically connects one electrical end of coil L to the other end of the coil), to thereby theoretically force the voltage, V, on coil L to be zero, though practically (e.g., due to electrical characteristics of the switches), it may be approximately zero (e.g., less than a threshold value; e.g., less than 1 volt). From equation (1) above it follows that di/dt is forced to be zero as well (di/dt=0), which means that the coil's current is theoretically kept constant. (The coil's current may change a little due to power/energy that is dissipated by the resistance of the coil.) Closing switches S3 and S4 short circuits coil L and, as a result of this, creates a closed current loop I3 that comports with the coil's current at the time when switching circuit 400 transitions or switches from the current control mode to the current hold mode. ('Comport with' means the magnitude and direction of current I3 are identical to the magnitude and direction of the coil's current, be it I1 or I2, as the case may be, at the time when switching circuit 400 transitions or switches from the current control mode to the current hold mode.)

The controller may be configured to, during the current control mode period, alternate the voltage polarity of the voltage, which is provided to the coil, by concurrently, at substantially the same time or in overlapping time, or simultaneously closing the first and fourth switches (e.g., switches S1 and S4) and opening the second and third switches (e.g., switches S2 and S3), then concurrently, at substantially the same time or in overlapping time, or simultaneously (or at about the same time) opening the first and fourth switches (e.g., switches S1 and S4) and closing the second and third switches (e.g., switches S2 and S3), and to iterate this sequence as many times as required or calculated from or based on, for example, a magnetic maneuvering force required during, or for, each current control mode period. The controller may be configured to iterate this 'alternating voltage polarity' sequence for as long as the switching circuit is to remain in the current control mode of operation. The controller may be configured to alternate the voltage polarity of the voltage source provided to the electrical coil (L) by using a pulse width modulation (PWM) scheme, or any other suitable scheme.

The controller may be configured, during the current hold mode period (during the second period), to completely disconnect the electrical coil from the power source by concurrently, at substantially the same time or in overlapping time, or simultaneously opening the first and second switches (e.g., switches S1 and S2), or one of them (if the other is already open) and closing the third and fourth switches (e.g., switches S3 and S4) to thereby close an electrical current loop (e.g., current loop I3) via (a loop that includes) the electrical coil L.

Figure 5A:
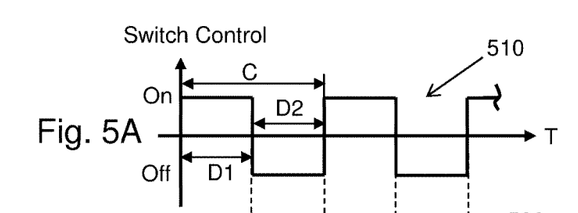
FIGS. 5A-5C show PWM related signals according to an embodiment of the invention.
Figure 5B:
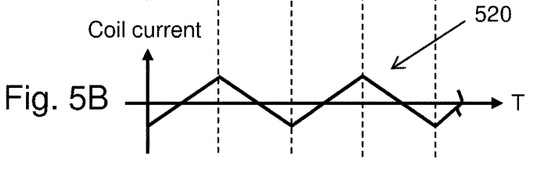
Figure 5C:
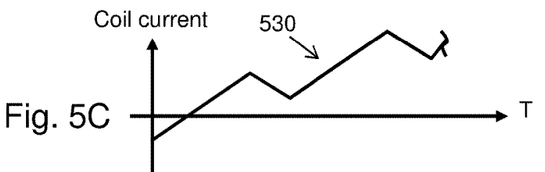

FIGS. 5A, 5B and 5C show typical signals involved in PWM control schemes; they demonstrate control of a coil's current by using PWM scheme according to an embodiment of the present invention. FIG. 5A shows a switch control signal 510 (as a function of time) that includes cycles such as cycle C. Each cycle may have an "On" period (e.g., "On" period D1) and an "Off" period (e.g., "Off" period D2). Operating a switching circuit, for example switching circuit 400, in a current control mode may be implemented, for example, by providing a control signal similar to control signal 510 to the switches of the switching circuit. More specifically, a current control mode may be implemented, for example, by closing a pair of 'anti-symmetrical' switches (e.g., switches pair S1 and S4) and at, and for, the same time opening the opposite anti-symmetrical switches (e.g., switches pair S2 and S3) whenever signal 510 is at the "On" state, and, conversely, closing the other/opposite anti-symmetrical pair of switches (e.g., pair S2 and S3) and opening switches S1 and S4 whenever signal 510 is at the "Off" state. Controlling a coil's current may be implemented by changing the duty cycle of signal 510. For example, signal 510 corresponds to 50% duty cycle, meaning that the "On" state in a cycle of signal 510 occupies one half of the cycle and the "Off" state occupies the other half of that cycle. (In other words, D1/C=0.50.)

Assume that each "On" pulse closes switches S1 and S4 and opens switched S2 and S3, each "Off" pulse opens switches S1 and S4 and closes switched S2 and S3, and the duty cycle is 50%, as shown in FIG. 5A. The current of the coil may be similar to signal 520 of FIG. 5B. That is, since the same current flows through the coil in opposite directions and for the same period of time (e.g., in one direction during period D1, then in the opposite direction during period D2, which, in this example, is equal to period D1), the coil's average current remains constant. However, if the duty cycle is greater than 50% (that is, D1/C>0.50), the coil's current increases with each cycle C of the switch control signal, as shown in FIG. 5C at 530. (The coil's current may be decrease by using a duty cycle less than 50% (that is, D1/C<0.50).

Figure 6:
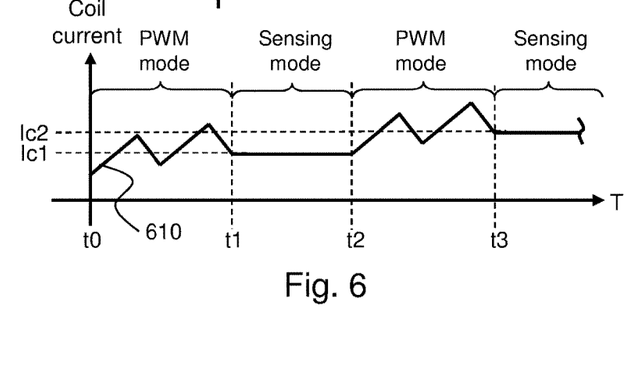
FIG. 6 show transitions between current control operation mode and current hold operation mode according to an embodiment of the invention.

FIG. 6 illustrates a coil's current 610 when a switching circuit (e.g., switching circuit 400) transitions or switches between current control mode of operation and current hold mode of operation. The terms 'current control mode' and 'PWM mode' are used herein interchangeably, though a coil's current may be controlled by using techniques other than PWM. The terms 'current hold mode' and 'sensing mode' are used herein interchangeably, though operations other than sensing localization signals by an in-vivo device may be executed when the device or system operated in this mode. The mode or state of the device may be alternated by, for example, repeatedly switching between states or modes.

During the time period t0-t1, the switching control (e.g., switching control 400) is operated in the current control mode, during which mode the coil's current may change as per a magnetic maneuvering requirement. (By way of example, the coil current 610 generally increases between times t0 and t1.) At time t1, the operation mode, or state, of the switching circuit transitions or switches from the current control mode to the current hold mode, during which mode the coil's current prior to the transition or switch is maintained. (In the example shown in FIG. 6, the coil's current is shown constant; e.g., having a value Ic1, between time t1 and time t2.)

At time t2, the operation mode, or state, of the switching circuit transitions or switches from the current hold mode to the current control mode, during which the coil's current is permitted to change according to a magnetic maneuvering requirement. (In the example shown in FIG. 6, the coil's current is shown increasing between times t2 and t3.) At time t3, the operation mode, or state, of the switching circuit transitions or switches from the current control mode to the current hold mode, during which the coil's current prior to the transition or switch is maintained. (In the example shown in FIG. 6, the coil's current is shown constant; e.g., having a value Ic2, from time t3 onwards.)

The coil's electrical current to be maintained (e.g., kept constant) during each particular current hold mode is the coil's electrical current at the time when the current control mode period preceding the particular current hold mode period ends, or the electrical current at the time of the pertinent transition or switch from the current control mode to the particular current hold mode, or shortly before the pertinent transition time. Since the direction of the coil's current changes during each current control mode period, the switching circuit used to control the coil's current (e.g., switching circuit 400) is operated such that both magnitude and direction of the coil's current at the end of each particular current control mode period are maintained during the current hold mode period following the particular current control mode. (FIG. 6 does not show the direction of the coil's current, though it can be inferred from the slopes of current 610; that is, the positive slopes indicate a first direction while the negative slopes indicate a second direction which is opposite the first direction.) The time length of any "PWM mode" period and of any "Sensing mode" period (e.g., periods t0-t1, t1-t2 and t2-t3, and successive periods) may be fixed/constant or variable. Time length of a period, or a ratio between adjacent periods, may be set per application.

Figure 7:
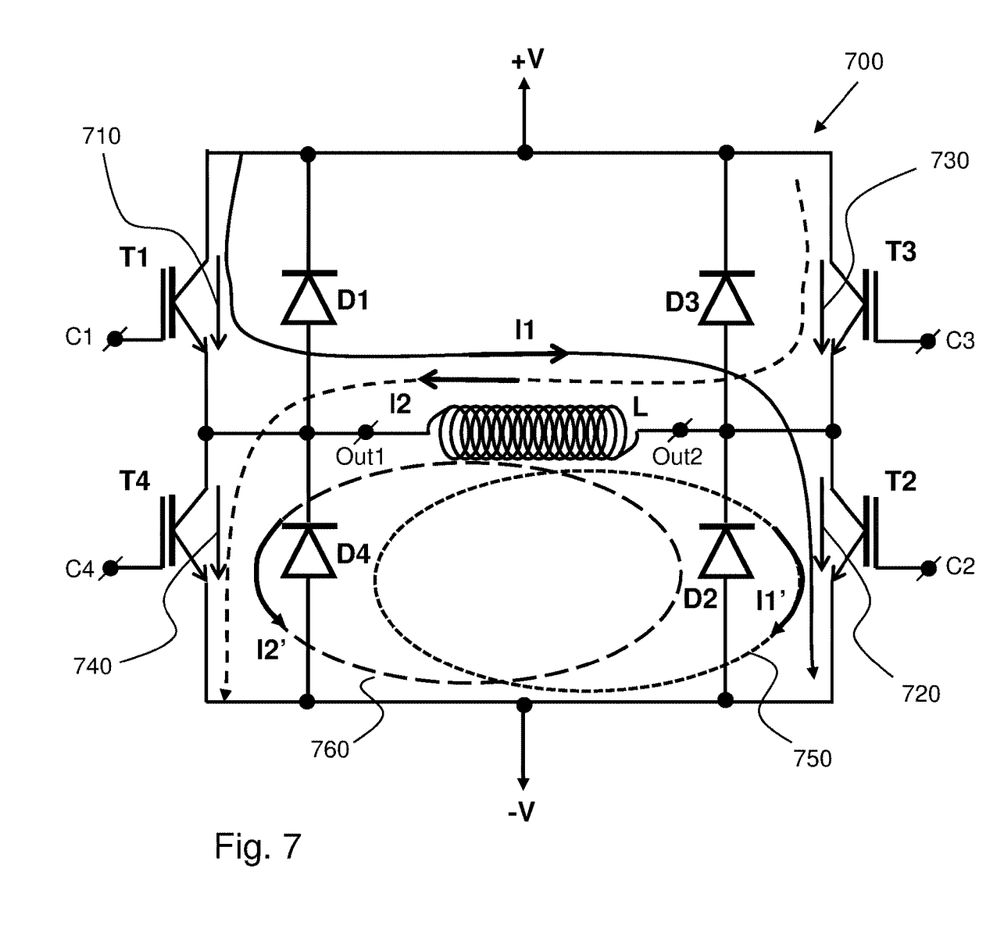
FIG. 7 shows a switching circuit according to an embodiment of the invention.

FIG. 7 schematically illustrates an example implementation of a switching circuit. Switching circuit 700 may include four transistors, designated as T1, T2, T3 and T4, where each transistor functions (is operated) as a switch. For example, transistor T1 may function as switch S1 of FIG. 4, transistor T2 may function as switch S4 of FIG. 4, etc. Switches may be devices other than transistors, or single transistors. Each transistor has a control input, C. For example, transistor T1 has a control input C1, transistor T2 has a control input C2, etc. Each transistor may controllably be in conductive state in which it has low impedance (so it may pass electrical current), or in cutoff state in which it has high impedance (so it cannot pass electrical current). Each transistor, if in the conducting state, can pass an electrical current in the direction shown in FIG. 7: transistor T1 can pass current in direction 710, transistor T2 can pass current in direction 720, transistor T3 can pass current in direction 730 and transistor T4 can pass current in direction 740. Switching circuit 700 may have four control input terminals (C1, C2, C3 and C4) for controlling operation of the switching circuit, and two output terminals, designated as Out1 and Out2 that are connected to electrical coil L. Switching circuit 700 may also include diodes, for example four diodes which are designated as D1, D2, D3 and D4. A switch may include only one electrical component (e.g., a transistor), or more than one component; e.g., two components (e.g., a transistor and a diode). Each of transistors T1 through T4 may have a protective diode associated with it; to protect the associated transistor from high reversed voltage that coil L may develop. Transistor T1 may have associated with it diode D1, transistor T2 may have associated with it diode D2, transistor T3 may have associated with it diode 3, and transistor T4 may have associated with it diode D4.

A particular transistor (Ti) may be configured to sustain an electrical current in a first direction in the electrical coil (L) during periods in which the current control mode is activated, and a diode associated with the particular transistor may be configured to sustain an electrical current loop in a second direction via the electrical coil during periods in which the current hold mode is activated, where the second direction is different than the first direction. By way of example, a diode (e.g., D2, D4) may be used to close an electrical current loop (e.g., loop I1' via D4, loop I2' via D2) via coil L when the conduction direction of the associated transistor is opposite to the direction of the loop's current. A 'switch' may, therefore, include a transistor to sustain a coil's current in a first direction when the current control mode is used (and the hold mode is deactivated), and a diode to sustain a coil's 'loop' current in a second direction when the current hold mode is used (and the control mode is deactivated), where the second direction is opposite to the first direction. For example, transistor T2 and diode D2 form, make up or jointly define a controllable switch that enables (i) an electrical current (current I1) during current control mode periods and (ii) a coil's loop current (loop current I2') during current hold mode periods. Transistor T4 and diode D4 form, make up or jointly define a controllable switch that enables an electrical current (current I2) during current control mode periods and a coil's loop current (loop current I1') during current hold mode periods.

Operating switching circuit 700 may be implemented by a controller controlling, during a first period corresponding to a current control mode, switching circuit 700 to alternate a voltage polarity of the voltage source provided to electrical coil L, to thereby control a magnitude and direction of the electrical current of the electrical coil, and by controlling switching circuit 700, during a second period different from the first period and corresponding to a current hold mode, to disconnect electrical coil L from the voltage source and, instead, to short-circuit the electrical coil to maintain the magnitude and direction of the coil's electrical current at the end of the first period. For example, the controller may, during the first period, or current control mode, provide an "on" control signal to control terminals C1 and C2 to transition transistors T1 and T2 into, or to maintain the conductive state and, simultaneously, an "off" control signal to control terminals C3 and C4 to transition transistors T3 and T4 into, or to maintain the cutoff state, to thereby obtain a current IL Then (when it is time to change the direction of the current of the coil, still during the first period), the controller may, during the second period, or current hold mode, provide an "off" control signal to control terminals C1 and C2 to transition transistors T1 and T2 into the cutoff state and, simultaneously, an "on" control signal to control terminals C3 and C4 to transition transistors T3 and T4 into the "on" state, to thereby obtain a current I2 which may be identical or similar to current I1 but flows in the opposite direction. During the first period, the controller may provide a signal similar to control signal 510 to control terminals C1 through C4 to operate switching circuit 700 in the current control mode, and change the signal's duty cycle to change the current of coil L.

The controller may transition switching circuit 700 from the current control mode to the current hold mode by providing a control signal to control terminals C1 and C3 to transition (or maintain) transistors T1 and T3 into the cutoff state, to thereby disconnect coil L from the voltage source, and by simultaneously providing a control signal to control terminals C2 and C4, to transition (or maintain) transistors T2 and T4 into the "on" state, to thereby enable a current loop I1 ', or I2', through coil L ('or'—depending on the direction of coil's current at the transition time). (I1' is direction-wise identical to current I1 and have a similar value as current I1; I2' is direction-wise identical to current I2 and have a similar value as current I2.)

Since electrical current can flow in transistors T2 and T4 only in the directions respectively shown at 720 and 740, current loop IF can be closed via transistor T2 and diode D4, and current loop I2' can be closed via transistor T4 and diode D2, as shown in FIG. 7 by ellipses 750 and 760, respectively. Theoretically, if there were no losses in switching circuit 700, IF would have been equal to I1, and I2' would have been equal to I2. However, due to losses in the circuit, for example in the form of heat dissipation, the current flowing through coil L during the current hold mode period decreases gradually. Nevertheless, since the current's gradual decrease is known in advance, this phenomenon may be dealt with satisfactorily. In addition, in many applications the current hold mode may be used for relatively short periods and, in such cases, the coil's current decrease is practically insignificant.

A switch used in the switching circuit may be an insulated-gate bipolar transistor ("IGBT"). The insulated-gate bipolar transistor, or IGBT, is a three-terminal power transistor combining high efficiency and fast switching capability. Since it is designed to turn on and off rapidly, such devices are often used with pulse width modulation.

Figure 8:
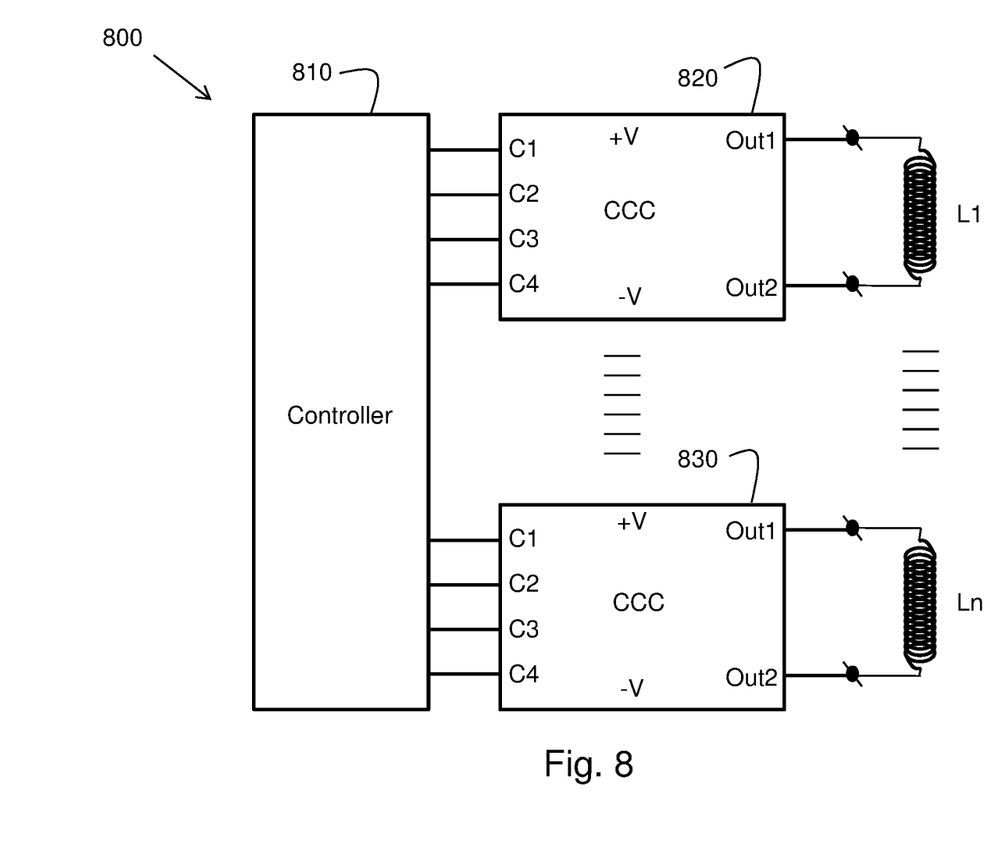
FIG. 8 shows an electromagnetic field maneuvering system according to an embodiment of the invention.

FIG. 8 schematically illustrates a switching control system 800 for generating a magnetic maneuvering force for maneuvering, for example, an in-vivo device such as in-vivo device 110 or 206. Switching control system 800 may include a computer processor or controller 810 and a number n of coil control circuits ("CCCs") 820 to 830 for controlling the electrical current of n coils, designated as L1 . . . Ln. Each CCC may include a switching circuit similar to switching circuit 400 or 700, or function in a similar way as switching circuit 400 or 700. Controller 810 may individually operate each of the n CCCs in the way described herein, for example, in connection with switching circuits 400 and 700, according to an operation cycle (e.g., cycle C in FIG. 5A).

Controller 810 may, for example, operate CCCs in a current control mode to control the magnetic maneuvering force(s) that maneuver the in-vivo device, and in the current hold mode to maintain the magnetic maneuvering force(s) at a value, or values, that it/they may have at the transition time when the switching circuit switches from the current control mode to the current hold mode. Controller 810 may, for example, operate the switching circuit, or switching function, of each CCC, in each operation cycle, during a first period to control a magnetic maneuvering force to maneuver an in-vivo device within an operating region, and during a second period to maintain the magnetic maneuvering force at a value prior to the transition to the second period. The second period may overlap a sensing window of the in-vivo device during which the in-vivo device may sense one or more localization signals.

Controller 810 may apply/activate the current control mode of operation to control a magnetic force applied to a magnetically maneuverable device (e.g., MSU) 211 of FIG. 2), and the current hold mode of operation to enable (another system) sensing of electromagnetic signals (e.g., by SCA 210 of FIG. 2) for determining the location and/or orientation of the maneuverable device. Controller 810 may be configured to carry out embodiments of methods disclosed herein for example, by executing software or instructions.

Figure 9:
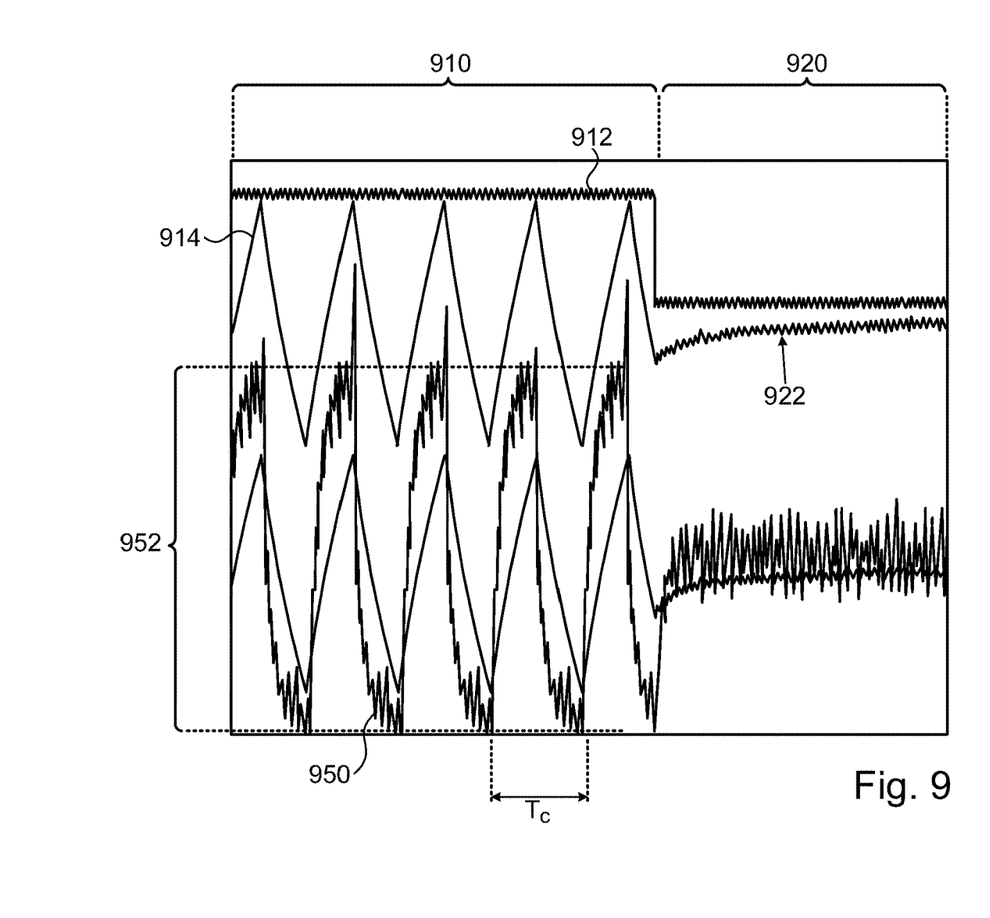
FIG. 9 depicts signal traces in accordance with an embodiment of the invention.

FIG. 9 depicts example signal traces according to an example embodiment of the invention. Assume that the signal traces are derived from, or representing, signals in an in-vivo system including an in-vivo device, a localization system for transmitting localization signals to the in-vivo device, and a magnetic field maneuvering system for maneuvering the in-vivo device. Referring to FIG. 9, a signal 912 may be a signal indicating to the in-vivo device, localization system and maneuvering system when magnetic maneuvering signals are generated by the maneuvering system, and when the localization system can transmit the localization signals.

During time period 910, the maneuvering system generates magnetic field maneuvering signals to maneuver the in-vivo device. Signal 914 is a coil current generated by the magnetic field maneuvering system during the current control mode (e.g., during period 910). Coil current 914 comports with a current control mode period during which coil's current 914 is controlled using, for example, a PWM control signal. Coil's current 914 is, therefore, a saw-tooth signal comporting with the frequency and duty cycle of the PWM control signal.

Time period 920 is a current hold mode period during which the coil's current is to be maintained constant. During time period 920 the maneuvering system stops generating the magnetic field maneuvering signals and the localization system transmits a localization signal to the in-vivo device, in order for it to be sensed by/in the in-vivo device. As shown in FIG. 9, coil current 914 is substantially constant during period 920 (a current holding mode period), as shown at 922, as opposed to coil current 914 that alternately changes during current control mode period 910.

Signal 950 represents a localization signal that is sensed by the in-vivo device. Usually, localization signals are to be transmitted to the in-vivo device only during period 920 (e.g., when no device maneuvering is performed). However, for the sake of comparison, localization signal was transmitted to the in-vivo device also during the time when the maneuvering system generated the saw-tooth coil current, in order to assess the electromagnetic field interference induced by it in the localization signal sensing coil(s). As shown in FIG. 9, the electromagnetic field interference induced in the sensing coils of the in-vivo device during normal operation of the maneuvering system (when the current control mode is used) results in a noisy signal (950)

with a relatively large amplitude (952) and with a dominant frequency, F (F=1/Tc), that equals the PWM's switching frequency. However, during the current hold operation mode, when the PWM is shut down and the switching circuit transitions into the current hold operation mode (during period 920), the noise due to the coil's current is cancelled out, leaving noises that are filterable more easily.

Figure 10:
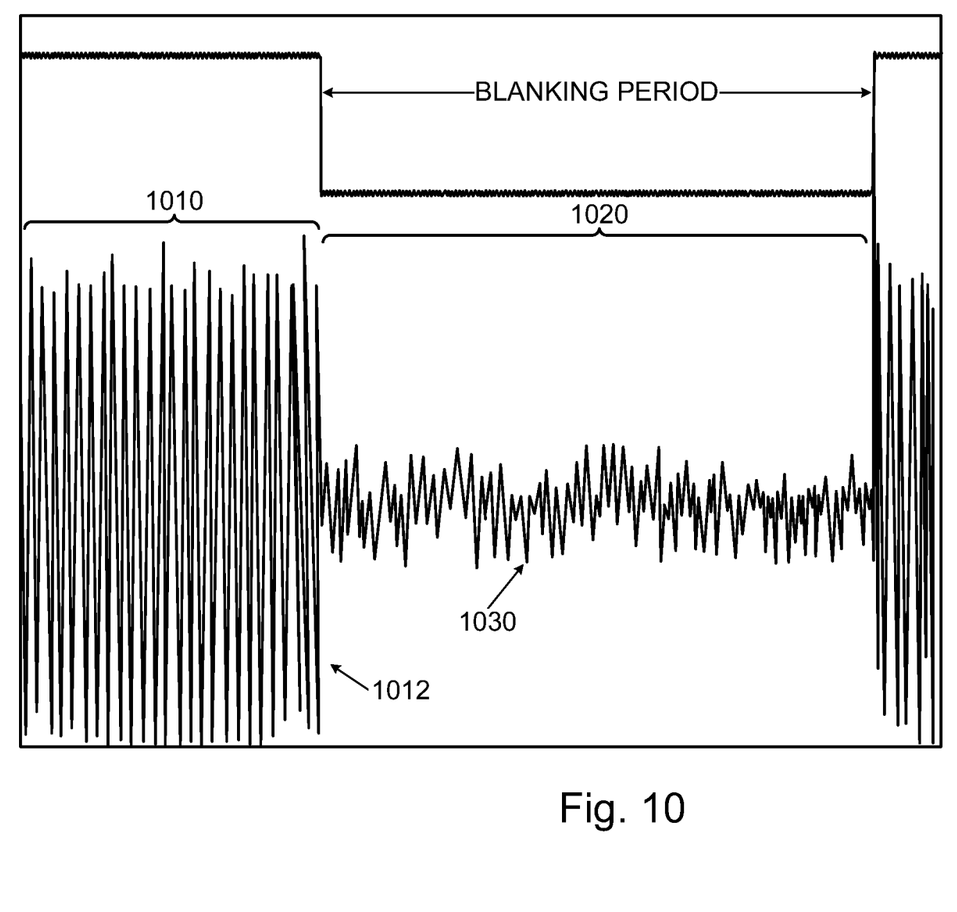
FIG. 10 depicts additional signal traces in accordance with an embodiment of the invention.

FIG. 10 depicts signal traces according to an example embodiment of the invention. During a current control mode of operation 1010, a localization sensing coil of an in-vivo device may sense a very noisy signal (1012) due to the maneuvering system operating the maneuvering coils (e.g., by using PWM) during that period. However, during the current hold operation mode period 1020, the localization sensing coil of the in-vivo device may sense a significantly lower noise (1030).

Figure 11:
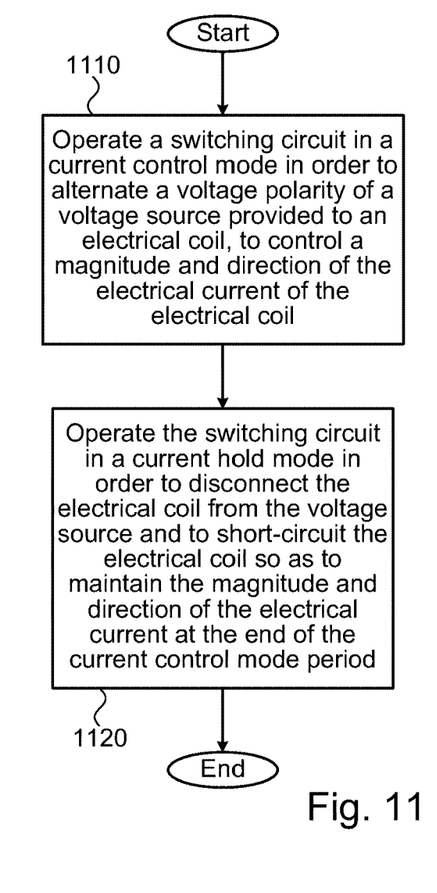
FIG. 11 depicts a method for operating a switching circuit according to an embodiment of the invention.

FIG. 11 depicts a method for operating a switching circuit for controlling an electrical current of an electrical coil according to an example embodiment of the invention. Assume that an electrical coil is connected to a voltage source via a switching circuit. At step 1110, the switching circuit may be controlled during a first period, or in a current control mode period, to alternate a voltage polarity of the voltage source provided to the electrical coil, to thereby control a magnitude and direction of the electrical current of the electrical coil. At step 1120, the switching circuit may be controlled during a second period different from the first period, or in a current hold mode period, to disconnect the electrical coil from the voltage source and to short-circuit the electrical coil so as to maintain the magnitude and direction of the electrical current at the end of the first period (e.g., at the transition time when the switching circuit transitions from the first period or current control mode, to the second period or current hold mode). (Other, or different, sequences of operations may be used.)

Operating the switching circuit in the first period, or in the current control mode, enables controlling of an electromagnetic maneuvering force (generated; e.g., by MMU 140) that may maneuver an in-vivo device (e.g., in-vivo device 110), and operating the switching circuit in the second period, or in the current hold mode, may maintain the electromagnetic maneuvering force at a value it has at the transition time, when the switching circuit switches from the current control mode to the current hold mode.

As described above, an in-vivo device may sense a localization signal during a sensing window (e.g., sensing window 352, FIG. 3), and, as explained herein, it is expedient to mute the PWM switching in order not to superimpose a PWM's originated interference on the localization signals sensed by the in-vivo device during the sensing window. Therefore, the second period (the period during which the current hold mode is used or activated) may overlap a sensing window of the in-vivo device during which the in-vivo device may sense one or more localization signals.

The articles "a" and "an" are used herein to refer to one or to more than one (e.g., to at least one) of the grammatical object of the article, depending on the context. By way of example, depending on the context, "an element" can mean one element or more than one element. The term "including" is used herein to mean, and is used interchangeably with, the phrase "including but not limited to". The terms "or" and "and" are used herein to mean, and are used interchangeably with, the term "and/or," unless context clearly indicates otherwise. The term "such as" is used herein to mean, and is used interchangeably, with the phrase "such as but not limited to".

Different embodiments are disclosed herein. Features of certain embodiments may be combined with features of other embodiments; thus certain embodiments may be combinations of features of other or multiple embodiments. Embodiments of the invention may include an article such as a computer or processor non-transitory storage medium, such as for example a memory, a disk drive, or a USB flash memory, encoding, including or storing instructions, e.g., computer-executable instructions, which when executed by a processor or controller, carry out methods disclosed herein. For example, a system may include a non-transitory storage medium such as storage unit 240, computer-executable instructions and a controller such as controller 260 or 810. Some embodiments may be provided in a computer program product that may include a non-transitory machine-readable medium, having stored thereon instructions, which may be used to program a computer, or other programmable devices, to perform methods as disclosed above. Having thus described exemplary embodiments of the invention, it will be apparent to those skilled in the art that modifications of the disclosed embodiments will be within the scope of the invention. Alternative embodiments may, accordingly, include more modules, fewer modules and/or functionally equivalent modules. The present disclosure is relevant to various types of in-vivo devices (e.g., in-vivo devices with one or more imagers, in-vivo devices with no imagers at all, etc.), to various types of receivers, and to various types of magnetic maneuvering systems. Hence the scope of the claims that follow is not limited by the disclosure herein.

The invention claimed is:

1. A method for controlling an electrical current of an electrical coil, comprising:
   for the electrical coil connected to a voltage source via a switching circuit, transitioning a state of the switching circuit between,
      a current control mode of operation in which the switching circuit alternates a voltage polarity of the voltage source to thereby control a magnitude and direction of an electrical current of the electrical coil, and
      a current hold mode of operation in which the switching circuit disconnects the electrical coil from the voltage source and short-circuits the electrical coil to maintain the magnitude and direction of the electrical current of the electrical coil at a transition time between the current control mode and the current hold mode.

2. The method as in claim 1, wherein operating the current control mode is to control a magnetic maneuvering force to maneuver an in-vivo device, and operating the current hold mode is to maintain the magnetic maneuvering force at a value it has at the transition time, when the switching circuit switches from the current control mode to the current hold mode.

3. The method as in claim 2, comprising applying the current hold mode during a sensing window of the in-vivo device during which the in-vivo device senses a localization signal.

4. The method as in claim 1, wherein alternating the state of the switching circuit is by using pulse width modulation (PWM) scheme.

5. The method as in claim 1, comprising applying the current control mode of operation to control a magnetic force applied to a magnetically maneuverable device, and the current hold mode of operation to enable sensing of electromagnetic signals for determining the location and/or orientation of the maneuverable device.

6. A method for controlling an electrical current state of an electrical coil, comprising:
for the electrical coil connected to a voltage source via a switching circuit,
controlling, during a first period, the switching circuit to alternate a voltage polarity of the voltage source provided to the electrical coil, to thereby control a magnitude and direction of the electrical current of the electrical coil; and
controlling, during a second period different from the first period, the switching circuit to disconnect the electrical coil from the voltage source and to short-circuit the electrical coil to maintain the magnitude and direction of the electrical current at the end of the first period.

7. The method as in claim 6, wherein controlling the switching circuit during the first period is to control a magnetic maneuvering force maneuvering an in-vivo device within an operating region, and controlling the switching circuit during the second period is to maintain the magnetic maneuvering force at a value prior to the transition to the second period.

8. The method as in claim 6, wherein the second period overlaps a sensing window of the in-vivo device during which the in-vivo device senses a localization signal.

9. The method as in claim 6, comprising alternating the state of the switching circuit is by using a pulse width modulation (PWM) scheme.

10. A system for controlling an electrical current of an electrical coil, comprising:
a switching circuit comprising:
a first switch and a second switch respectively interposed between a first terminal and a second terminal of the electrical coil and a positive terminal of a voltage source powering the electrical coil;
a third switch and a fourth switch respectively interposed between the first terminal and the second terminal of the electrical coil and a negative terminal of the voltage source; and
a controller to switch the switching circuit between a current control mode and a current hold mode, said controller configured to:
control the switching circuit during a period of the current control mode to alternate a voltage polarity of the voltage source to thereby control a magnitude and direction of the electrical current of the electrical coil, and
control the switching circuit during a period of the current hold mode to disconnect the electrical coil from the voltage source and to short-circuit the electrical coil to maintain the magnitude and direction of the electrical current at the time when the controller switches the switching circuit from the current control mode to the current hold mode.

11. The system as in claim 10, wherein the controller is configured, during the current control mode period, to alternate the voltage polarity of the voltage by simultaneously closing the first and fourth switches and opening the second and third switches, then simultaneously opening the first and fourth switches and closing the second and third switches, and to iterate this sequence.

12. The system as in claim 10, wherein the controller is configured, during the current hold mode period, to simultaneously open the first and second switches and close the third and fourth switches, to thereby close an electrical current loop including the electrical coil.

13. The system as in claim 10, wherein the controller is configured to alternate the voltage polarity of the voltage source provided to the electrical coil by using a pulse width modulation scheme.

14. The system as in claim 10, wherein each of the first switch, the second switch, the third switch and the forth switch comprises a transistor.

15. The system as in claim 14, wherein with each transistor is associated a diode.

16. The system as in claim 15, wherein a particular transistor is configured to sustain an electrical current in a first direction in the electrical coil during periods in which the current control mode is activated, and the diode associated with the particular transistor is configured to sustain an electrical current loop in a second direction via the electrical coil during periods in which the current hold mode is activated, wherein the second direction is different than the first direction.

17. The system as in claim 10, wherein the controller is configured to activate the current control mode to control a magnetic force applied to a magnetically maneuverable device, and the current hold mode to facilitate sensing of electromagnetic signals for determining the location and/or orientation of the maneuverable device.

* * * * *